US012678025B2

(12) United States Patent　(10) Patent No.:　US 12,678,025 B2
Goto　(45) Date of Patent:　Jul. 14, 2026

(54) ENDOSCOPE IMAGE PROCESSING APPARATUS, ENDOSCOPE IMAGE PROCESSING METHOD, AND ENDOSCOPE IMAGE PROCESSING PROGRAM FOR SCENE RECOGNITION

(71) Applicant: FUJIFILM Corporation, Tokyo (JP)

(72) Inventor: Misaki Goto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 362 days.

(21) Appl. No.: 18/463,269

(22) Filed: Sep. 7, 2023

(65) Prior Publication Data

US 2023/0414066 A1　Dec. 28, 2023

Related U.S. Application Data

(63) Continuation of application No. PCT/JP2022/009339, filed on Mar. 4, 2022.

(30) Foreign Application Priority Data

Mar. 9, 2021　(JP) ................................. 2021-037107

(51) Int. Cl.
*A61B 1/00*　(2006.01)
*G06T 7/00*　(2017.01)
(Continued)

(52) U.S. Cl.
CPC ...... *A61B 1/000096* (2022.02); *G06T 7/0012* (2013.01); *G06V 10/764* (2022.01);
(Continued)

(58) Field of Classification Search
CPC ......... A61B 1/000096; G06V 2201/03; G06V 2201/031
See application file for complete search history.

(56) References Cited

U.S. PATENT DOCUMENTS 11,934,491 B1 *　3/2024　Gilinsky ................ G06N 20/00
2015/0003700 A1　1/2015　Tani
(Continued)

FOREIGN PATENT DOCUMENTS

JP　　2015008781　　1/2015
JP　　2016054794　　4/2016
(Continued)

OTHER PUBLICATIONS

"International Search Report (Form PCT/ISA/210) of PCT/JP2022/009339", mailed on May 24, 2022, with English translation thereof, pp. 1-5.
(Continued)

*Primary Examiner* — Peter K Huntsinger
(74) *Attorney, Agent, or Firm* — JCIPRNET

(57)　　ABSTRACT

In an endoscope image processing apparatus including a processor, the processor is configured to execute: an endoscope image acquiring process of acquiring a time-series endoscope image; a scene recognizing process of recognizing a scene based on the endoscope image; a scene-recognition-result retaining process of causing a retaining unit to retain a scene recognition result of the recognized scene; a magnification information acquiring process of acquiring magnification information from an endoscope system or the endoscope image, the magnification information being related to a magnification ratio of the endoscope image or whether or not the endoscope image is magnified; and an output control process of controlling and outputting the scene recognition result retained in the retaining unit based on the acquired magnification information.

17 Claims, 10 Drawing Sheets

(51) Int. Cl.
    G06V 10/764     (2022.01)
    G06V 10/82     (2022.01)

(52) U.S. Cl.
    CPC .......... G06V 10/82 (2022.01); *G06V 2201/03* (2022.01); *G06V 2201/031* (2022.01)

(56) References Cited

U.S. PATENT DOCUMENTS

| | | |
|---|---|---|
| 2019/0311476 A1 | 10/2019 | Hayami et al. |
| 2019/0370971 A1 | 12/2019 | Saikou et al. |
| 2021/0153730 A1 | 5/2021 | Karino |
| 2021/0343011 A1 | 11/2021 | Kamon |
| 2022/0133214 A1 | 5/2022 | Shino |
| 2024/0087723 A1* | 3/2024 | Matsumura ........... G06T 7/0012 |

FOREIGN PATENT DOCUMENTS

| | | |
|---|---|---|
| JP | 2017213097 | 12/2017 |
| WO | 2018105063 | 6/2018 |
| WO | 2018158817 | 9/2018 |
| WO | 2020036121 | 2/2020 |
| WO | 2020162275 | 8/2020 |
| WO | 2020166247 | 8/2020 |

OTHER PUBLICATIONS

"Written Opinion of the International Searching Authority (Form PCT/ISA/237) of PCT/JP2022/009339", mailed on May 24, 2022, with English translation thereof, pp. 1-9.
"Notice of Reasons for Refusal of Japan Counterpart Application", issued on Oct. 14, 2025, with English translation 1 thereof, p. 1-p. 9.

* cited by examiner

[NORMAL OBSERVATION]        [MAGNIFIED OBSERVATION]

[NORMAL OBSERVATION]

[MAGNIFIED OBSERVATION]

[NORMAL OBSERVATION]

[MAGNIFIED OBSERVATION]

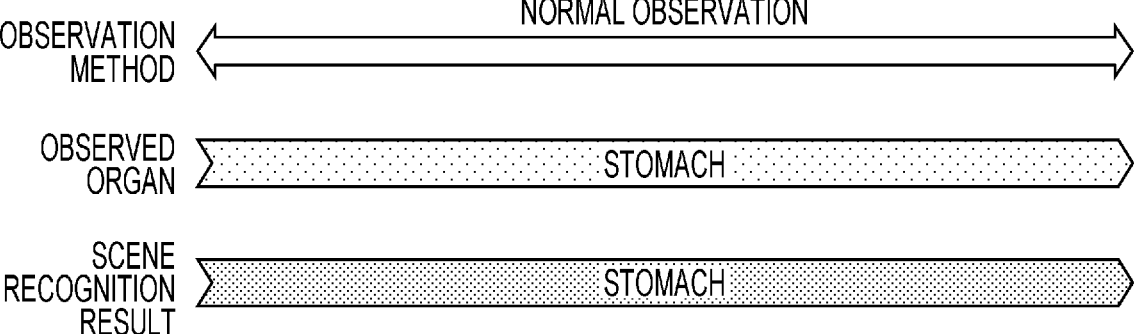

| OBSERVATION METHOD | ← NORMAL OBSERVATION → |
| OBSERVED ORGAN | STOMACH |
| SCENE RECOGNITION RESULT | STOMACH |

FIG. 9

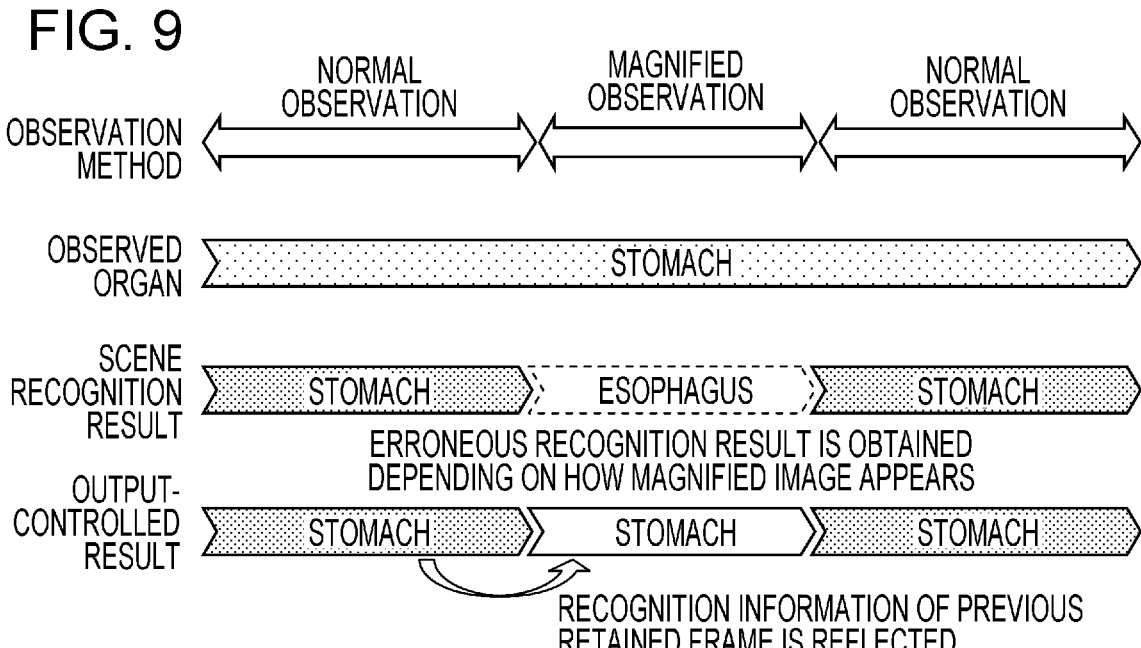

OBSERVATION METHOD: NORMAL OBSERVATION | MAGNIFIED OBSERVATION | NORMAL OBSERVATION

OBSERVED ORGAN: STOMACH

SCENE RECOGNITION RESULT: STOMACH | ESOPHAGUS | STOMACH

ERRONEOUS RECOGNITION RESULT IS OBTAINED DEPENDING ON HOW MAGNIFIED IMAGE APPEARS

OUTPUT-CONTROLLED RESULT: STOMACH | STOMACH | STOMACH

RECOGNITION INFORMATION OF PREVIOUS RETAINED FRAME IS REFLECTED

FIG. 10

| SCENE RECOGNITION RESULT | DUODENUM | | STOMACH | ESOPHAGUS | STOMACH | ESOPHAGUS |
|---|---|---|---|---|---|---|
| MAGNIFICATION ON/OFF INFORMATION | OFF | | OFF | ON | ON | ON |

→ TIME

FIG. 11

| TYPE OF ORGAN | RELIABILITY LEVEL (SCORE) | | | | | |
|---|---|---|---|---|---|---|
| PHARYNX | 10 | | 5 | 15 | 15 | |
| ESOPHAGUS | 15 | | 15 | 20 | 35 | |
| STOMACH | 60 | | 65 | 40 | 30 | |
| DUODENUM | 15 | | 15 | 25 | 20 | |
| MAGNIFICATION ON/OFF INFORMATION | OFF | | OFF | ON | ON | |

→ TIME

ENDOSCOPE IMAGE PROCESSING APPARATUS, ENDOSCOPE IMAGE PROCESSING METHOD, AND ENDOSCOPE IMAGE PROCESSING PROGRAM FOR SCENE RECOGNITION

CROSS-REFERENCE TO RELATED APPLICATIONS

The present application is a Continuation of PCT International Application No. PCT/JP2022/009339 filed on Mar. 4, 2022 claiming priority under 35 U.S.C § 119(a) to Japanese Patent Application No. 2021-037107 filed on Mar. 9, 2021. Each of the above applications is hereby expressly incorporated by reference, in its entirety, into the present application.

BACKGROUND OF THE INVENTION

1. Field of the Invention

The present invention relates to endoscope image processing apparatuses, endoscope image processing methods, and endoscope image processing programs, and particularly, to a technology for controlling a scene recognition result obtained from an endoscope image.

2. Description of the Related Art

In the related art, JP2015-8781A proposes an endoscope apparatus capable of adaptively detecting an uneven section in accordance with an observation mode.

Because an amount of movement of a photographic subject varies depending on the observation mode (scene), the endoscope apparatus described in JP2015-8781A senses the observation mode (i.e., a screening observation mode or a magnified observation mode) from the amount of movement, selects known characteristic information suitable for the uneven section (i.e., a lesion) in the photographic subject as information indicating known characteristics related to the structure of the photographic subject in accordance with whether the observation mode is the screening observation mode or the magnified observation mode, and uses the selected known characteristic information to adaptively detect the uneven section in the photographic subject.

SUMMARY OF THE INVENTION

The endoscope apparatus described in JP2015-8781A is configured to adaptively detect the uneven section in the photographic subject in accordance with whether the observation mode is the screening observation mode or the magnified observation mode, but is not configured to control a scene recognition result obtained from an endoscope image in accordance with the observation mode.

Although a lesion is frequently examined by being magnified during an endoscopic examination, how a magnified image of the lesion appears greatly differs from an image during normal observation. In an endoscopic examination using a computer aided diagnosis (CAD) involving recognizing a scene of, for example, an organ or a site, the magnified image of the lesion may cause the performance of the CAD to deteriorate, such that an erroneous scene recognition result may possibly be output from the CAD.

The present invention has been made in view of these circumstances, and an object thereof is to provide an endoscope image processing apparatus, an endoscope image processing method, and an endoscope image processing program that can stably (and accurately) output a scene recognition result obtained from a time-series endoscope image regardless of the magnification ratio of the endoscope image.

In order to achieve the aforementioned object, a first aspect of the present invention provides an endoscope image processing apparatus including a processor. The processor is configured to execute: an endoscope image acquiring process of acquiring a time-series endoscope image; a scene recognizing process of recognizing a scene based on the endoscope image; a scene-recognition-result retaining process of causing a retaining unit to retain a scene recognition result of the recognized scene; a magnification information acquiring process of acquiring magnification information from an endoscope system or the endoscope image, the magnification information being related to a magnification ratio of the endoscope image or whether or not the endoscope image is magnified; and an output control process of controlling and outputting the scene recognition result retained in the retaining unit based on the acquired magnification information.

According to the first aspect of the present invention, although scenes are sequentially obtained based on time-series endoscope images, if the endoscope image to be scene-recognized is magnified, a scene recognition result of an endoscope image retained in the past in the retaining unit is controlled and output, so that a highly-accurate scene recognition result can be output even when the endoscope image is magnified.

Normally, the main purpose of a magnified observation mode is to observe an already found lesion in detail. Therefore, it is unlikely that a scene recognition result acquired during a normal observation mode prior to the magnification changes during the magnification. Thus, during the magnified observation mode of an endoscope, a scene recognition result obtained and retained prior to the magnification is output, so that a scene recognition result with higher recognition accuracy can be output.

In the endoscope image processing apparatus according to a second aspect of the present invention, the scene-recognition-result retaining process preferably causes the retaining unit to retain the magnification information together with the scene recognition result.

In the endoscope image processing apparatus according to a third aspect of the present invention, the scene-recognition-result retaining process preferably causes the retaining unit to retain the scene recognition result on a time-series basis.

In the endoscope image processing apparatus according to a fourth aspect of the present invention, the processor is preferably configured to perform a process of generating a display image in which the magnification information is added to a specific position other than a display region of the endoscope image, and the magnification information acquiring process preferably acquires the magnification information by reading the magnification information at the specific position from the display image.

The magnification information of the current endoscope image may be displayed by being added to a specific position other than the display region of the endoscope image. A user can check the magnification ratio of the current endoscope image based on the displayed magnification information. In the magnification information acquiring process, the magnification information can be acquired by reading the magnification information at the specific position from the display image.

In the endoscope image processing apparatus according to a fifth aspect of the present invention, the magnification information acquiring process preferably acquires the magnification information from the processor.

The fourth aspect of the present invention is different from the fifth aspect of the present invention in that the magnification information is acquired by reading the magnification information at the specific position from the display image, whereas the magnification information is acquired directly from the processor in the fifth aspect of the present invention.

In the endoscope image processing apparatus according to a sixth aspect of the present invention, the output control process preferably sets a scene recognition result to be ultimately output from the scene recognition result retained in the retaining unit. The scene recognition result to be ultimately output is set based on the magnification information and a method for setting the scene recognition result. The magnification information and the method for setting the scene recognition result may be set in advance or may be selected by the user.

In the endoscope image processing apparatus according to a seventh aspect of the present invention, if the endoscope image is determined as being observed in a magnified mode based on the magnification information, the output control process preferably outputs a scene recognition result retained in the retaining unit and corresponding to when the endoscope image is determined as being not observed in the magnified mode. This is because a scene recognition result obtained based on a non-magnified endoscope image has higher recognition accuracy than a scene recognition result obtained based on a magnified endoscope image.

In the endoscope image processing apparatus according to an eighth aspect of the present invention, the output control process preferably outputs a latest scene recognition result retained in the retaining unit when the endoscope image is determined as being not observed in a magnified mode based on the magnification information.

In the endoscope image processing apparatus according to a ninth aspect of the present invention, the scene-recognition-result retaining process preferably causes the retaining unit to retain the scene recognition result on a time-series basis. The scene recognition result includes a reliability level for each of a plurality of scenes. The output control process preferably outputs, as the scene recognition result, a scene to which a highest reliability level of the reliability levels of the respective scenes belongs. The scene is retained in the retaining unit when the endoscope image is determined as not being observed in a magnified mode based on the magnification information.

In the endoscope image processing apparatus according to a tenth aspect of the present invention, the scene-recognition-result retaining process preferably causes the retaining unit to retain the scene recognition result on a time-series basis. The scene recognition result includes a reliability level for each of a plurality of scenes. The output control process preferably calculates an average value of reliability levels for each scene and outputs, as the scene recognition result, a scene to which a largest average value of the average values belongs. The scene is retained in the retaining unit when the endoscope image is determined as not being observed in a magnified mode based on the magnification information. If the current endoscope image is observed in the magnified mode, the scene recognition result may be output in the above-described manner. If the current endoscope image is not observed in the magnified mode, an average value of the reliability levels may be calculated for each scene by including the reliability level of the current scene retained in the retaining unit, and the scene to which the largest average value of the average values belongs may be output as the scene recognition result. Accordingly, the scene recognition result can be output accurately and stably.

In the endoscope image processing apparatus according to an eleventh aspect of the present invention, the scene-recognition-result retaining process preferably causes the retaining unit to retain the scene recognition result on a time-series basis. The scene recognition result includes a reliability level for each of a plurality of scenes. The output control process preferably reduces a weight of the reliability level corresponding to when the endoscope image is determined as being observed in a magnified mode based on the magnification information among the reliability levels of the respective scenes retained on the time-series basis in the retaining unit, calculates an average load value of the reliability level of each scene, and outputs, as the scene recognition result, a scene to which a largest average load value of the average load values belongs.

According to the eleventh aspect of the present invention, in addition to the reliability level of each scene when the endoscope image is determined as being not observed in the magnified mode, the reliability level of each scene when the endoscope image is determined as being observed in the magnified mode can be reflected on the scene recognition result by reducing the weight of the reliability level thereof. With respect to the reliability level of each scene when the endoscope image is determined as not being observed in the magnified mode, the weight may be sequentially reduced from the latest reliability level toward a past reliability level.

In the endoscope image processing apparatus according to a twelfth aspect of the present invention, the scene-recognition-result retaining process preferably provides an upper limit for a retained number of scene recognition results obtained in the scene recognizing process and retained in the retaining unit, and deletes a scene recognition result retained in the retaining unit, starting from an older scene recognition result, when the retained number exceeds the upper limit. This is because, if an upper limit is not provided for the retained number, a scene recognition result retained in the retaining unit may include a scene different from the current original scene.

In the endoscope image processing apparatus according to a thirteenth aspect of the present invention, the scene recognizing process preferably recognizes, based on the endoscope image, at least one of a type of an organ within a body, a section of an organ within a body, presence or absence of *Helicobacter pylori*, a range diagnosis of a lesion, image quality, or whether or not an image is appropriate for an image diagnosis.

A fourteenth aspect of the present invention provides an endoscope image processing method for causing a processor to execute a process including: a step for acquiring a time-series endoscope image; a scene recognizing step for recognizing a scene based on the endoscope image; a scene-recognition-result retaining step for causing a retaining unit to retain a scene recognition result of the recognized scene; a magnification information acquiring step for acquiring magnification information from an endoscope system or the endoscope image, the magnification information being related to a magnification ratio of the endoscope image or whether or not the endoscope image is magnified; and an output control step for controlling and outputting the scene recognition result retained in the retaining unit based on the acquired magnification information.

In the endoscope image processing method according to a fifteenth aspect of the present invention, the scene-recognition-result retaining step preferably causes the retaining unit to retain the magnification information together with the scene recognition result.

In the endoscope image processing method according to a sixteenth aspect of the present invention, the scene-recognition-result retaining step preferably causes the retaining unit to retain the scene recognition result on a time-series basis.

Preferably, the endoscope image processing method according to a seventeenth aspect of the present invention further includes a step for generating a display image in which the magnification information is added to a specific position other than a display region of the endoscope image. The magnification information acquiring step preferably acquires the magnification information by reading the magnification information at the specific position from the display image.

Preferably, the endoscope image processing method according to an eighteenth aspect of the present invention further includes a step for generating a display image in which the magnification information is added to a specific position other than a display region of the endoscope image. The magnification information acquiring step preferably acquires the magnification information from the processor that adds the magnification information to the display image.

In the endoscope image processing method according to a nineteenth aspect of the present invention, the output control step preferably sets a scene recognition result to be ultimately output from the scene recognition result retained in the retaining unit, the scene recognition result being set based on the magnification information and a method for setting the scene recognition result.

A twentieth aspect of the present invention provides an endoscope image processing program causing a processor to execute the steps in the endoscope image processing method according to any one of the fourteenth to nineteenth aspects of the present invention.

According to the present invention, a scene recognition result obtained from a time-series endoscope image can be stably (and accurately) output regardless of the magnification ratio of the endoscope image.

BRIEF DESCRIPTION OF THE DRAWINGS

FIG. 7 is a functional block diagram illustrating a first embodiment of output control performed by the output control unit;

FIG. 8 is a timing chart illustrating an actually observed organ and a scene recognition result in an observation method during the normal observation mode;

FIG. 9 is a timing chart illustrating an actually observed organ, a scene recognition result, and an output-controlled scene recognition result in an observation method having a mixture of the normal observation mode and the magnified observation mode;

FIG. 10 illustrates a first embodiment of, for example, scene recognition results retained in a memory;

FIG. 11 illustrates a second embodiment of, for example, scene recognition results retained in the memory.

DESCRIPTION OF THE PREFERRED EMBODIMENTS

Preferred embodiments of an endoscope image processing apparatus, an endoscope image processing method, and an endoscope image processing program according to the present invention will be described below with reference to the appended drawings.

Figure 1:
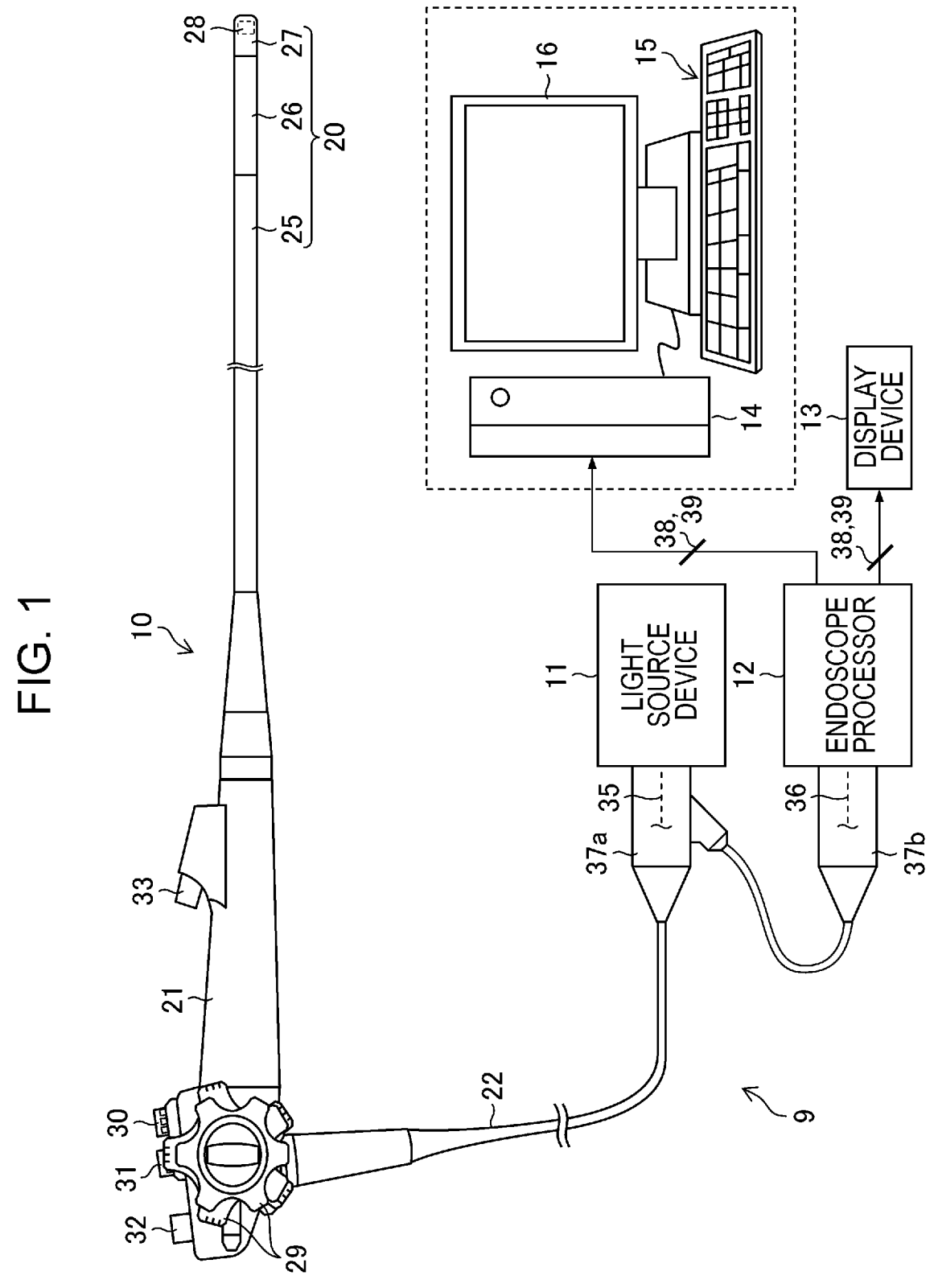
FIG. 1 is a schematic diagram illustrating the overall configuration of an endoscope system including an endoscope image processing apparatus according to the present invention.

Overall Configuration of Endoscope System Including Endoscope Image Processing Apparatus FIG. 1 is a schematic diagram illustrating the overall configuration of an endoscope system including an endoscope image processing apparatus according to the present invention.

As illustrated in FIG. 1, an endoscope system 9 includes an endoscope 10 serving as an electronic endoscope, a light source device 11, an endoscope processor 12, a display device 13, an endoscope image processing apparatus 14, an operating unit 15, and a display unit 16.

The endoscope 10 is configured to capture a time-series endoscope image including a photographic subject image, and is, for example, an upper gastrointestinal scope. The endoscope 10 has an insertion section 20 that is to be inserted into a subject (e.g., the pharynx, esophagus, stomach, or duodenum as a hollow organ) and that has a distal end and a base end, a handheld operation section 21 that is connected to the base end of the insertion section 20 and that is used for performing various operations by being held by a doctor as a surgeon, and a universal cord 22 connected to the handheld operation section 21.

The insertion section 20 entirely has a long and narrow shape. The insertion section 20 has a soft part 25, a bending part 26, and a tip part 27 that are connected in that order from the base end toward the distal end. The soft part 25 has flexibility. The bending part 26 is bendable in accordance with an operation performed using the handheld operation section 21. The tip part 27 contains therein, for example, an imaging optical system (objective lens) (not illustrated) and an imaging element 28.

The imaging element 28 is a complementary metal oxide semiconductor (CMOS) imaging element or a charge coupled device (CCD) imaging element. An imaging surface of the imaging element 28 receives image light of an observation site via an observation window (not illustrated) provided at a tip end surface of the tip part 27 and via an objective lens (not illustrated) disposed rearward of the observation window. The imaging element 28 picks up an image of the image light of the observation site received by the imaging surface (i.e., converts the image light into an electric signal), and outputs an image pick-up signal.

The handheld operation section 21 is provided with various types of operating members to be operated by a doctor (user). In detail, the handheld operation section 21 is provided with two types of bending knobs 29 used for bending the bending part 26, an air/water supply button 30 for an air/water supplying operation, and a suction button 31 for a suction operation. The handheld operation section 21 is also provided with a still-image capture command part 32 and a treatment tool inlet 33. The still-image capture command part 32 is used for giving a command for capturing a still image 39 of the observation site. The treatment tool inlet 33 is used for inserting a treatment tool (not illustrated) into a treatment-tool insertion path (not illustrated) extending through the insertion section 20.

The universal cord 22 is a connection cord for connecting the endoscope 10 to the light source device 11. The universal cord 22 contains a light guide 35, a signal cable 36, and a fluid tube (not illustrated) that extend through the insertion section 20. An end of the universal cord 22 is provided with a connector 37a connected to the light source device 11 and a connector 37b bifurcated from the connector 37a and connected to the endoscope processor 12.

By connecting the connector 37a to the light source device 11, the light guide 35 and the fluid tube (not illustrated) are inserted into the light source device 11. Accordingly, the endoscope 10 is supplied with required illumination light, water, and gas from the light source device 11 via the light guide 35 and the fluid tube (not illustrated). As a result, the illumination light is radiated toward the observation site from an illumination window (not illustrated) at the tip end surface of the tip part 27. Further, gas or water is injected from an air/water supply nozzle (not illustrated) at the tip end surface of the tip part 27 toward the observation window (not illustrated) at the tip end surface in accordance with a pressing operation performed on the aforementioned air/water supply button 30.

By connecting the connector 37b to the endoscope processor 12, the signal cable 36 and the endoscope processor 12 are electrically connected to each other. Accordingly, the image pick-up signal of the observation site is output from the imaging element 28 of the endoscope 10 to the endoscope processor 12 via the signal cable 36, and a control signal is output from the endoscope processor 12 to the endoscope 10 via the signal cable 36.

The light source device 11 supplies the illumination light to the light guide 35 of the endoscope 10 via the connector 37a. With regard to the illumination light, light in any of various wavelength ranges, such as white light (i.e., light in the white wavelength range or light in a plurality of wavelength ranges), light in at least one specific wavelength range, or a combination of the above, is selected in accordance with the purpose of the observation.

The endoscope processor 12 controls the operation of the endoscope 10 via the connector 37b and the signal cable 36. Based on the image pick-up signal acquired from the imaging element 28 of the endoscope 10 via the connector 37b and the signal cable 36, the endoscope processor 12 generates an image (also referred to as "motion picture 38") constituted of time-series endoscope images 38a including a photographic subject image. Further, if the still-image capture command part 32 is operated at the handheld operation section 21 of the endoscope 10, the endoscope processor 12 sets one of endoscope images in the motion picture 38 as the still image 39 in accordance with the capture command timing, concurrently with the generation of the motion picture 38.

The motion picture 38 and the still image 39 are endoscope images picked up within a subject, that is, a living body. Furthermore, if the motion picture 38 and the still image 39 are images obtained from light (special light) in the aforementioned specific wavelength range, the two images are special light images. The endoscope processor 12 outputs the generated motion picture 38 and the generated still image 39 to the display device 13 and the endoscope image processing apparatus 14.

The endoscope processor 12 may generate (acquire) a special light image having information about the aforementioned specific wavelength range based on a normal light image obtained from the aforementioned white light. In this case, the endoscope processor 12 functions as a special-light-image acquisition unit. Then, the endoscope processor 12 obtains a signal of the specific wavelength range by performing a calculation based on color information about red, green, and blue (RGB) colors or cyan, magenta, and yellow (CMY) colors included in the normal light image.

Furthermore, the endoscope processor 12 may generate a feature quantity image, such as a known oxygen saturation image, based on, for example, at least one of the normal light image obtained from the aforementioned white light or the special light image obtained from the light (special light) in the aforementioned specific wavelength range. In this case, the endoscope processor 12 functions as a feature-quantity-image generating unit. The motion picture 38 or the still image 39, including the living-body image, the normal light image, the special light image, and the feature quantity image mentioned above, is an endoscope image obtained by converting an image pick-up result or a measurement result of the human body for the purpose of image-based diagnosis or examination into an image.

The display device 13 is connected to the endoscope processor 12, and functions as a display unit that displays the motion picture 38 and the still image 39 input from the endoscope processor 12. The doctor (user) moves the insertion section 20 forward and backward while checking the motion picture 38 displayed on the display device 13. If the doctor (user) finds, for example, a lesion in the observation site, the doctor (user) operates the still-image capture command part 32 to execute a still-image pick-up process on the observation site, or performs a treatment, such as a diagnosis or a biopsy.

The endoscope system 9 in this example has a zoom function for magnifying the endoscope image in response to an operation performed on a zoom button (zoom operation section) (not illustrated) provided at the handheld operation section 21. Examples of the zoom function include electronic zooming involving electronically magnifying the endoscope image output from the imaging element 28 by changing the thinning-out rate thereof, optical zooming involving optically magnifying the endoscope image by using an objective lens as a zoom lens, and zooming using both zooming techniques (i.e., zooming involving magnifying the endoscope image by optical zooming and then further magnifying the endoscope image by electronic zooming when the magnification ratio in the optical zooming reaches a maximum).

Accordingly, when a hollow organ is observed with a relatively wide angle (e.g., 90° or larger) (normal observation) and a region-of-interest, such as a lesion candidate, is found, the region-of-interest can be observed in a magnified mode (magnified observation).

Endoscope Image Processing Apparatus

The endoscope image processing apparatus 14 recognizes the scene of, for example, an organ or a site based on a time-series endoscope image, retains a scene recognition result, and controls and outputs the retained scene recognition result based on magnification information related to the magnification ratio of the endoscope image or whether or not the endoscope image is magnified. An example of the endoscope image processing apparatus 14 used in this embodiment is a personal computer.

The operating unit 15 includes, in addition to, for example, a keyboard and a mouse connected to the personal computer in a wired or wireless manner, buttons provided at the handheld operation section 21 of the endoscope 10. The display unit 16 used is any of various types of monitors, such as a liquid crystal monitor, connectable to the personal computer.

Endoscope Image Processing Apparatus According to Embodiment

Figure 2:
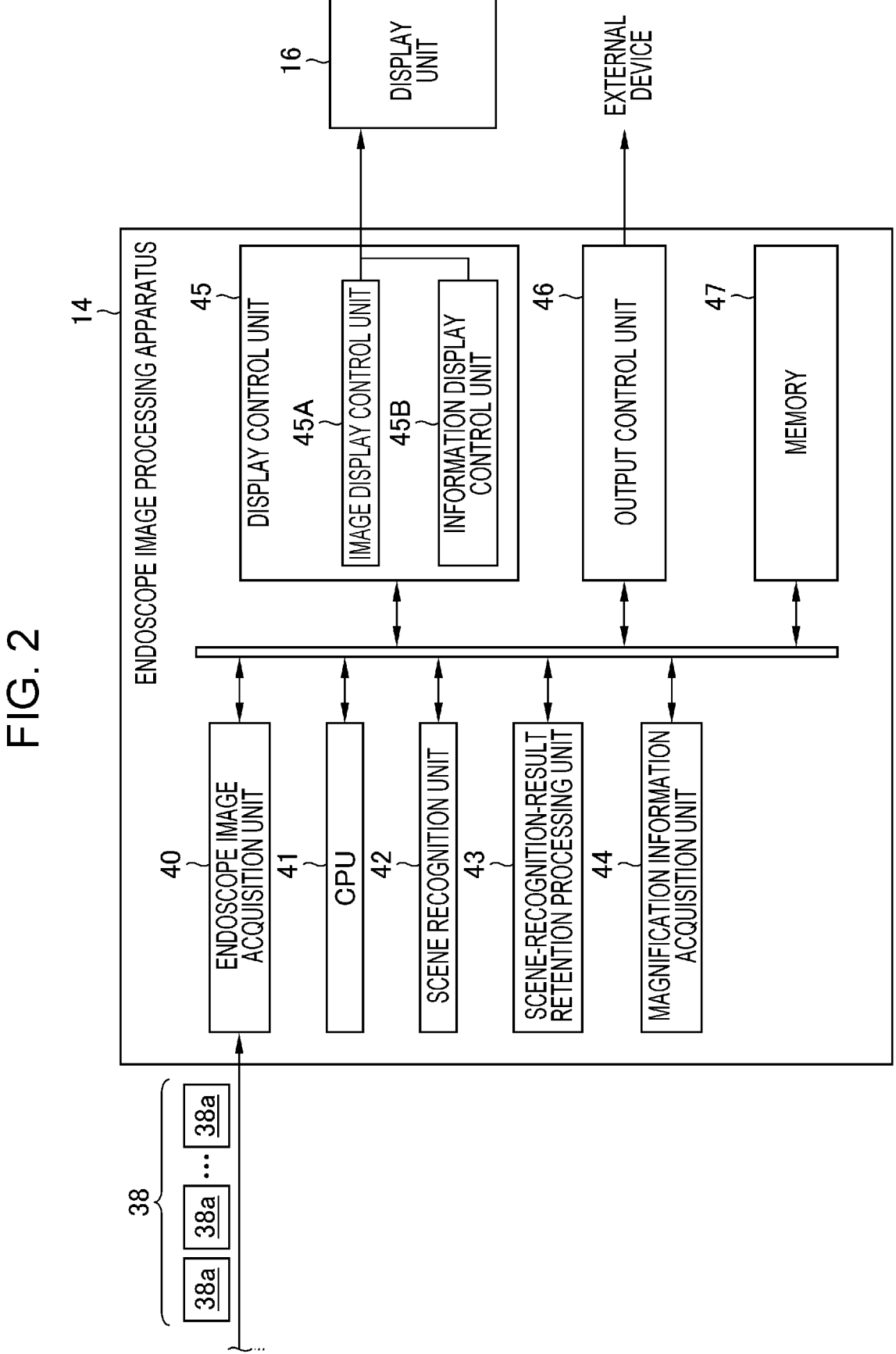
FIG. 2 is a block diagram illustrating the endoscope image processing apparatus according to an embodiment.

FIG. 2 is a block diagram illustrating the endoscope image processing apparatus according to an embodiment.

The endoscope image processing apparatus 14 illustrated in FIG. 2 includes an endoscope image acquisition unit 40, a central processing unit (CPU) 41, a scene recognition unit 42, a scene-recognition-result retention processing unit 43, a magnification information acquisition unit 44, a display control unit 45, an output control unit 46, and a memory 47. Processing in each unit is implemented by at least one processor.

The CPU 41 operates based on various types of programs including an operating system stored in the memory 47 and an endoscope image processing program according to the present invention, performs overall control of the endoscope image acquisition unit 40, the scene recognition unit 42, the scene-recognition-result retention processing unit 43, the magnification information acquisition unit 44, the display control unit 45, and the output control unit 46, and also functions as a part of each of these units.

The endoscope image acquisition unit 40 is an endoscope-image acquisition processing unit that sequentially acquires, as endoscope images, the time-series endoscope images 38a including the photographic subject image from the endoscope processor 12 by using an image input/output interface (not illustrated) connected to the endoscope processor 12 (FIG. 1) in a wired or wireless manner.

The scene recognition unit 42 performs a scene recognizing process involving recognizing the scene of each endoscope image based on the time-series endoscope images. In this example, the scene recognition unit 42 recognizes the type of hollow organ (e.g., the pharynx, esophagus, stomach, or duodenum) image-captured by the endoscope 10 serving as an upper gastrointestinal scope.

The scene recognition unit 42 includes, for example, a convolutional neural network (CNN) that calculates, for example, a feature quantity from each endoscope image 38a and performs a scene recognizing process on the endoscope image, and calculates a feature quantity by using, for example, color information within the endoscope image and a gradient of each pixel value. Based on the calculated feature quantity, the scene recognition unit 42 recognizes (classifies) the type of hollow organ captured as an endoscope image as any one of the "pharynx", "esophagus", "stomach", and "duodenum".

Figure 3:
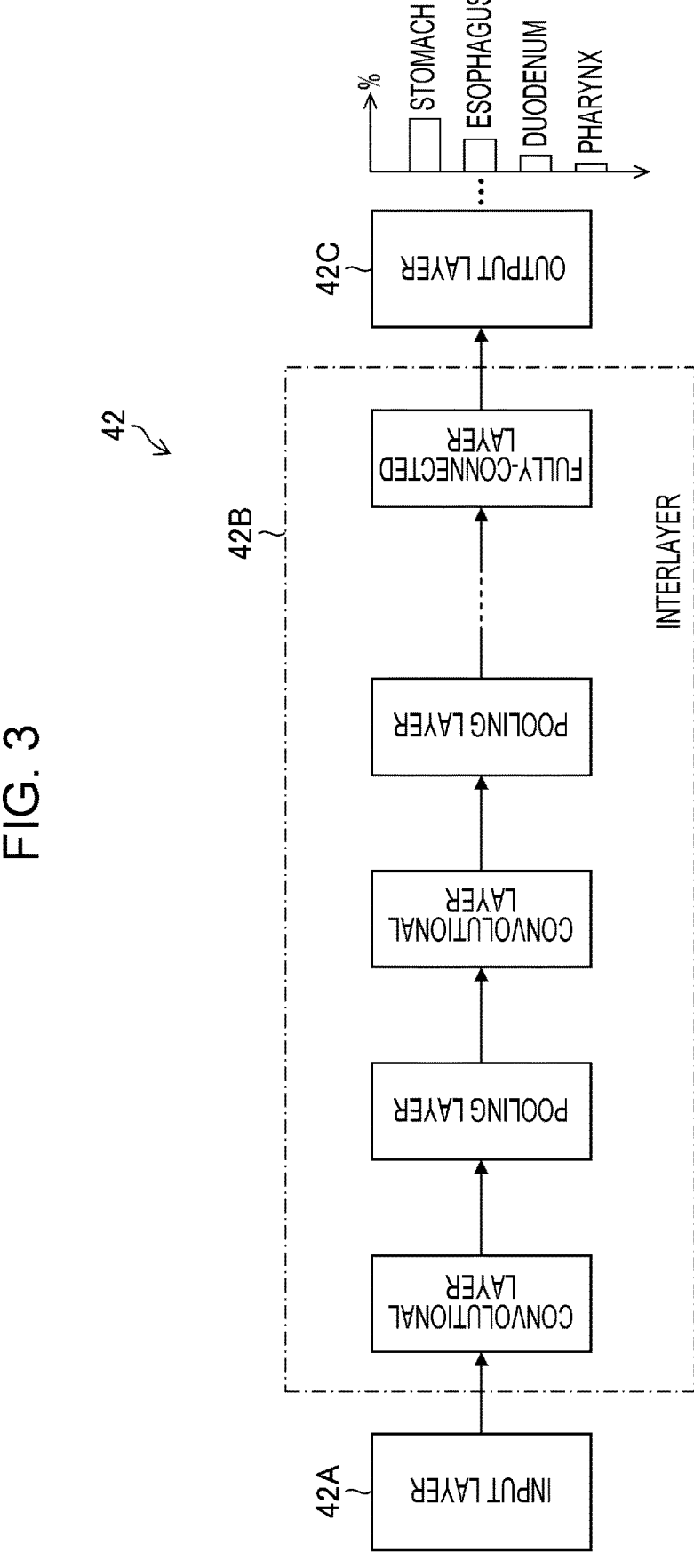
FIG. 3 illustrates a scene recognition unit according to an embodiment.

FIG. 3 illustrates a scene recognition unit according to an embodiment.

FIG. 3 schematically illustrates a representative configuration example of the CNN applied to the scene recognition unit 42.

As illustrated in FIG. 3, the scene recognition unit (CNN) 42 includes an input layer 42A, an interlayer 42B having multiple sets each including a convolutional layer and a pooling layer and also having a fully-connected layer, and an output layer 42C. Each layer has a structure in which multiple "nodes" are connected by an "edge".

The input layer 42A sequentially receives the endoscope images 38a constituting the motion picture 38.

The interlayer 42B has multiple sets each having a convolutional layer and a pooling layer, and also has a fully-connected layer. The interlayer 42B extracts a feature quantity from each endoscope image 38a input from the input layer. Each convolutional layer performs filtering on a nearby node in a previous layer (i.e., performs a convolutional arithmetic process using a filter), so as to acquire a "feature map". Each pooling layer reduces a feature map output from the convolutional layer, so as to obtain a new feature map. A "convolutional layer" has a role of performing feature extraction, such as edge extraction, from an image, and a "pooling layer" has a role of applying robustness to prevent the extracted feature from being affected by, for example, parallel translation.

The interlayer 42B is not limited to the case where each set has a convolutional layer and a pooling layer, and may include a case where the convolutional layers are successive or a case where the interlayer 42B includes a normalization layer.

The fully-connected layer is weighted-connected to all the nodes in the previous layer and outputs a value (i.e., a feature variable) converted using an activation function. In this example, the fully-connected layer outputs a feature variable for each of the scenes of the endoscope images 38a.

The output layer 42C functioning as an inference unit performs a conversion into a reliability level by using a softmax function based on the output (i.e., the feature variable) from the fully-connected layer, and calculates a reliability level (i.e., a score) for each scene. Since an image of any one of the "pharynx", "esophagus", "stomach", and "duodenum" is captured as an endoscope image 38a in this example, scene recognition of any of the four scenes of the "pharynx", "esophagus", "stomach", and "duodenum" is performed. The output layer 42C can output, as a scene recognition result, the scene with the highest reliability level among the reliability levels of the four scenes, or can output the reliability levels of the four respective scenes. The total of the reliability levels of the four respective scenes is 100%.

For example, a parameter of a filter used in each convolutional layer in the interlayer 42B and a weighting factor of the fully-connected layer are preliminarily optimized in accordance with multiple pieces of learning data. The scene recognition unit 42 is not limited to including the CNN, and may employ a recurrent neural network (RNN) often used for predicting time-series data.

Figures 4A, 4B:
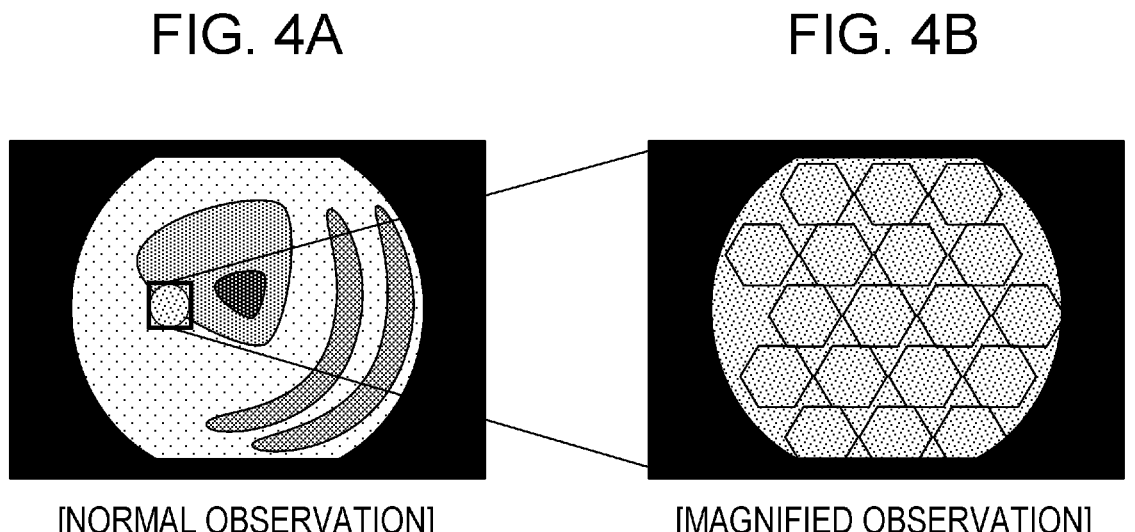
FIG. 4A and FIG. 4B illustrate examples of an endoscope image during a normal observation mode and an endoscope image during a magnified observation mode.

FIG. 4A and FIG. 4B illustrate examples of an endoscope image during a normal observation mode and an endoscope image during a magnified observation mode.

The scene recognition unit 42 has been trained by machine learning using multiple pieces of learning data each constituted of a pair of an endoscope image in the normal observation mode, as illustrated in FIG. 4A, and a ground truth scene.

Therefore, if the scene recognition unit 42 receives an endoscope image in the magnified observation mode, as illustrated in FIG. 4B, the scene recognition accuracy of the endoscope image decreases, as compared with the scene recognition accuracy in the normal observation mode.

The scene-recognition-result retention processing unit 43 causes the memory 47 functioning as a retaining unit to retain a scene recognition result of the endoscope image 38a obtained by the scene recognition unit 42. In this case, the scene-recognition-result retention processing unit 43 can cause the memory 47 to retain magnification information, to be described later, together with the scene recognition result, and can also cause the memory 47 to retain scene recognition results including reliability levels of multiple scenes (e.g., four scenes of the pharynx, esophagus, stomach, and duodenum) on a time-series basis.

The magnification information acquisition unit 44 acquires, from the endoscope system 9 or the endoscope image 38a, magnification information related to the magnification ratio of the endoscope image 38a or whether or not the endoscope image 38a is magnified.

When the zoom button is operated by the user for performing a zoom-up operation, the endoscope system 9 magnifies the endoscope image 38a in response to a zoom-up command input from the zoom button. An image display control unit 45A of the display control unit 45 generates a display image from the endoscope image 38a acquired by the endoscope image acquisition unit 40 and outputs the display image to the display unit 16 where the endoscope image 38a is displayed. In addition, the image display control unit 45A generates a display image in which magnification information (i.e., the magnification ratio or information indicating whether or not the endoscope image is magnified) of the endoscope image 38a is added to a specific position other than the display region of the endoscope image 38a.

Figure 5A:
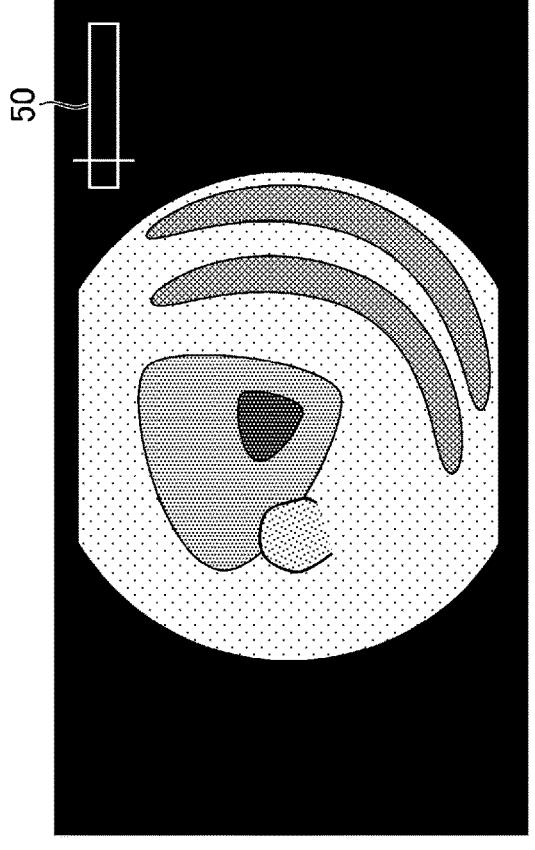
FIG. 5A and FIG. 5B illustrate a first display example during the normal observation mode and the magnified observation mode.
Figure 5B:
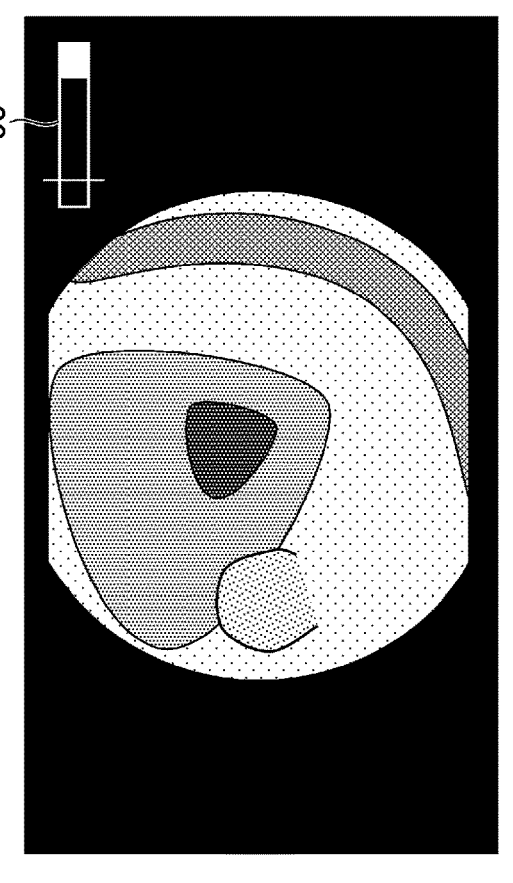

FIG. 5A and FIG. 5B illustrate a first display example during the normal observation mode and the magnified observation mode.

A magnification scale 50 in the first display example illustrated in FIG. 5A and FIG. displays the magnification ratio in a continuous manner. FIG. 5A illustrates a magnification ratio of 1× (i.e., the magnification ratio in the normal observation mode), and FIG. 5B illustrates a magnification ratio of approximately 3× (i.e., the magnification ratio in the magnified observation mode) when the maximum magnification ratio is set at, for example, 10×.

Figure 6A:
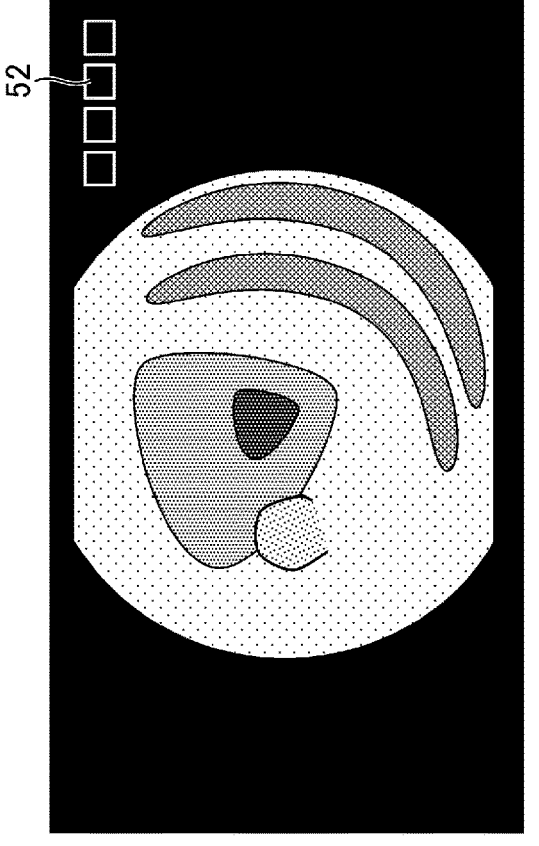
FIG. 6A and FIG. 6B illustrate a second display example during the normal observation mode and the magnified observation mode.
Figure 6B:
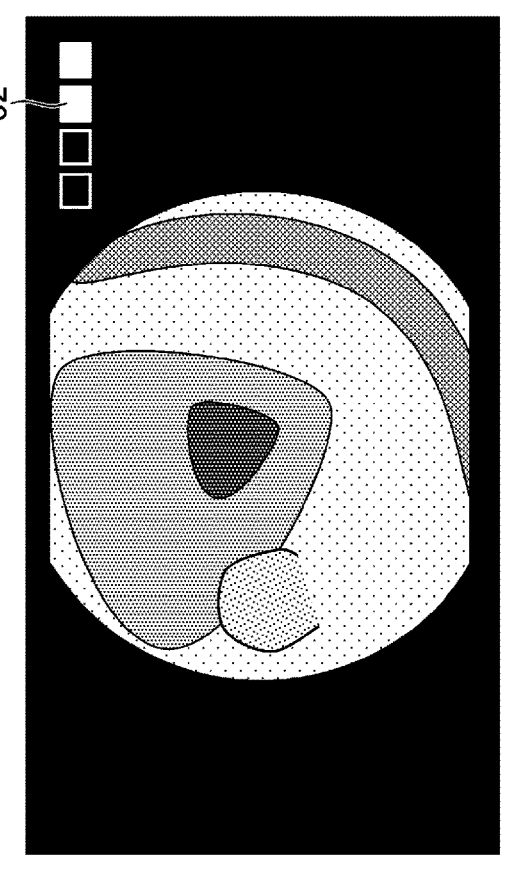

FIG. 6A and FIG. 6B illustrate a second display example during the normal observation mode and the magnified observation mode.

A magnification scale 52 in the second display example illustrated in FIG. 6A and FIG. 6B displays the magnification ratio in a stepwise manner. FIG. 6A illustrates a magnification ratio of 1× (i.e., the magnification ratio in the normal observation mode), and FIG. 6B illustrates a magnification ratio of 5× (i.e., the magnification ratio in the magnified observation mode) when the maximum magnification ratio is set at, for example, 10×.

Referring back to FIG. 2, the magnification information acquisition unit 44 can acquire the magnification information by reading the magnification information (i.e., the magnification scale 50 or 52 illustrated in FIG. 5A and FIG. 5B or FIG. 6A and FIG. 6B) at the specific position from the display image displayed on the display unit 16.

The magnification information acquisition unit 44 can also acquire the magnification information directly from the endoscope system 9. This is because the endoscope system 9 holds the magnification information for generating the display image in which the magnification information (i.e., the magnification scale 50 or 52 illustrated in FIG. 5A and FIG. 5B or FIG. 6A and FIG. 6B) is added to the specific position other than the display region of the endoscope image.

The display control unit 45 includes the image display control unit 45A and an information display control unit 45B.

The image display control unit 45A generates display images from the time-series endoscope images 38a acquired by the endoscope image acquisition unit 40 and outputs the generated display images to the display unit 16 where the endoscope images 38a (i.e., a motion picture) are sequentially displayed.

The information display control unit 45B causes the display unit 16 to display the scene recognition result, the magnification information, and other information. With regard to the scene recognition result, the information display control unit 45B causes the display unit 16 to display a scene recognition result output-controlled by the output control unit 46 to be described below.

The output control unit 46 performs an output control process involving controlling and outputting the scene recognition result retained in the memory 47 based on the magnification information acquired by the magnification information acquisition unit 44. The scene recognition result output-controlled by the output control unit 46 is output to an external device and is also used in the endoscope image processing apparatus 14. For example, when the scene recognition result is displayed on the display unit 16, the scene recognition result is used by the information display control unit 45B.

Output Control Process

First Embodiment of Output Control Process

Figure 7:
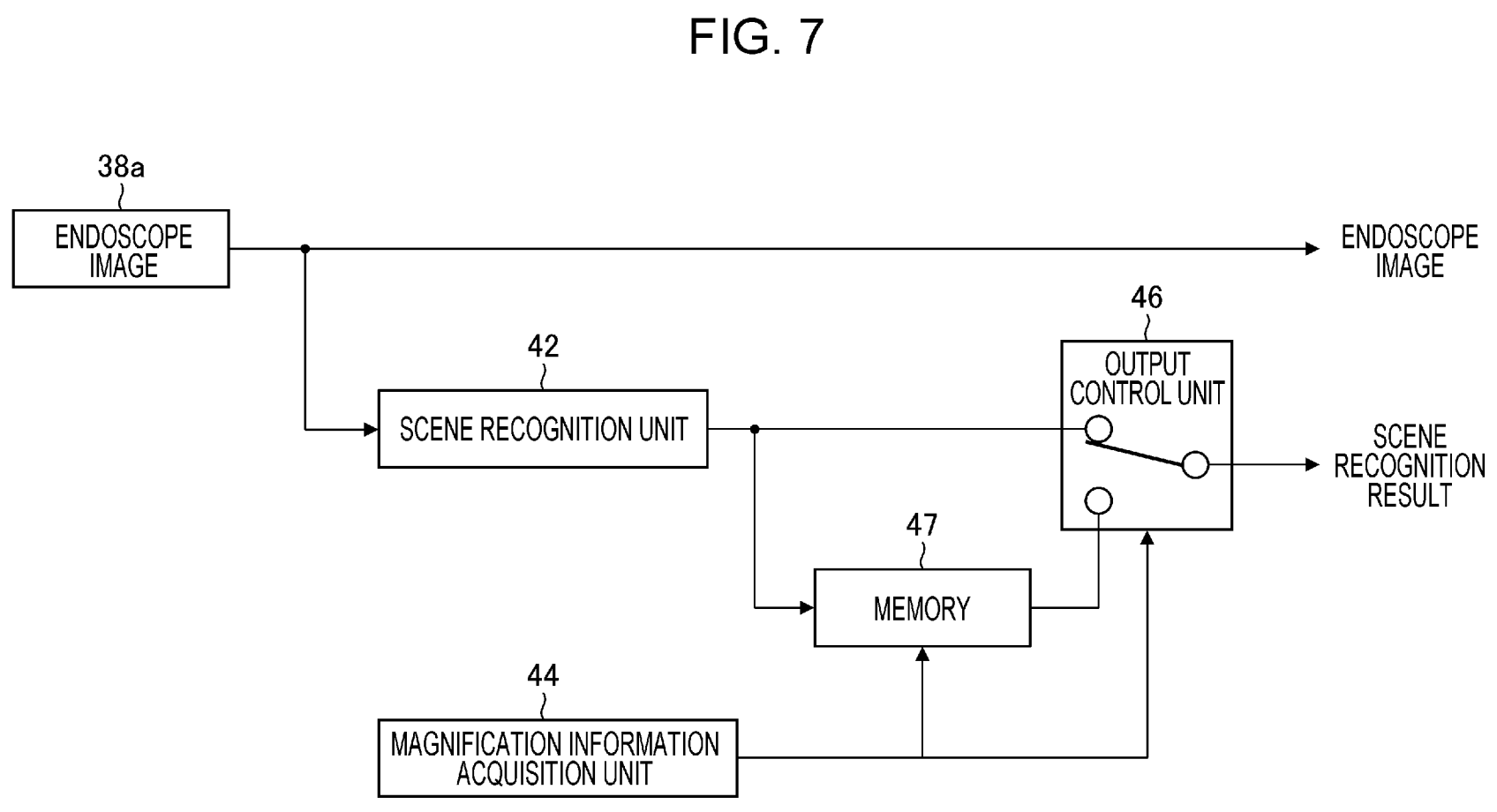

FIG. 7 is a functional block diagram illustrating a first embodiment of output control performed by the output control unit.

As illustrated in FIG. 7, each of the time-series endoscope images 38a is added to the scene recognition unit 42. The scene recognition unit 42 outputs a scene recognition result obtained based on the endoscope image 38a to the output control unit 46 and the memory 47.

In synchronization with each of the endoscope images 38a sequentially input to the scene recognition unit 42, the magnification information acquisition unit 44 acquires the magnification information of the endoscope image 38a. The magnification information can be acquired by reading the magnification information added to the specific position other than the display region of the endoscope image, as mentioned above, or can be acquired directly from the endoscope system 9.

The magnification information acquired by the magnification information acquisition unit 44 is output to the memory 47 and the output control unit 45.

If the magnification information input from the magnification information acquisition unit 44 corresponds to the normal observation mode, the memory 47 updates the stored scene recognition result in accordance with the scene recognition result added from the scene recognition unit 42. If the magnification information corresponds to the magnified observation mode, the memory 47 does not perform the update in accordance with the scene recognition result added from the scene recognition unit 42. Accordingly, the memory 47 retains the latest scene recognition result when normal observation is being performed.

The output control unit 46 outputs the scene recognition result output from the scene recognition unit 42 or the scene recognition result retained in the memory 47 in a switching manner based on the magnification information input from the magnification information acquisition unit 44, so as to perform output control of the scene recognition result.

If the magnification information input from the magnification information acquisition unit 44 corresponds to the normal observation mode, the output control unit 46 directly outputs the scene recognition result output from the scene recognition unit 42. If the magnification information input from the magnification information acquisition unit 44 corresponds to the magnified observation mode, the output control unit 46 switches to the scene recognition result retained in the memory 47 and outputs the scene recognition result.

When the magnification information acquisition unit 44 is to acquire the magnification information corresponding to the normal observation mode, the scene recognition result retained in the memory 47 is to be updated in accordance with the scene recognition result obtained by the scene recognition unit 42. Therefore, the output control unit 46 may output the scene recognition result retained in the memory 47 regardless of whether the magnification information corresponds to the normal observation mode or the magnified observation mode. In this case, as a result of the scene recognition result retained in the memory 47 being controlled based on the magnification information, the output control unit 46 controls and outputs the scene recognition result based on the magnification information.

FIG. 8 is a timing chart illustrating an actually observed organ and a scene recognition result in an observation method during the normal observation mode.

As illustrated in FIG. 8, the scene recognition unit 42 during the normal observation mode can output a scene recognition result (i.e., the type of organ) that matches the actually observed organ. In the example illustrated in FIG. 8, the actually observed organ in the normal observation mode is the "stomach", and the scene recognition result also indicates the "stomach". This is because the scene recognition unit 42 that receives the endoscope images 38*a* with the magnification ratio in the normal observation mode can accurately recognize the scene of each endoscope image 38*a*.

FIG. 9 is a timing chart illustrating an actually observed organ, a scene recognition result, and an output-controlled scene recognition result in an observation method having a mixture of the normal observation mode and the magnified observation mode.

As illustrated in FIG. 9, the actually observed organ is the "stomach". However, the scene recognition unit 42 recognizes the "stomach" as a scene recognition result during the normal observation mode and recognizes the "esophagus" as a scene recognition result during the magnified observation mode.

The reason why the scene recognition unit 42 erroneously obtains the scene recognition result during the magnified observation mode in this manner is because the scene recognition unit 42 has been trained by machine learning using a pair of an endoscope image with the magnification ratio in the normal observation mode and ground truth data as learning data. Specifically, when the scene recognition unit 42 receives an endoscope image with the magnification ratio in the magnified observation mode, the accuracy of the scene recognition result to be output is low.

With regard to the scene recognition result output-controlled by the output control unit 46, the scene recognition result retained in the memory 47 (i.e., the scene recognition result obtained during the normal observation mode) is used without using the scene recognition result obtained by the scene recognition unit 42 during the magnified observation mode.

Accordingly, the actually observed organ and the output-controlled scene recognition result can be matched.

Second Embodiment of Output Control Process

FIG. 10 illustrates a first embodiment of, for example, scene recognition results retained in the memory.

As illustrated in FIG. 10, the memory 47 retains scene recognition results and magnification information for the respective time-series endoscope images in association with each other in chronological order. In the example illustrated in FIG. 10, magnification on/off information indicating whether the mode involves magnification lower than a fixed value corresponding to the normal observation mode or magnification higher than or equal to the fixed value corresponding to the magnified observation mode is retained as the magnification information.

If the output control unit 46 performing the output control process according to the second embodiment determines that an endoscope image is being observed in a magnified mode based on the magnification information (magnification on/off information) acquired by the magnification information acquisition unit 44, the output control unit 46 outputs the scene recognition results retained in the memory 47 illustrated in FIG. 10 and corresponding to when the endoscope images are determined as being not observed in the magnified mode (i.e., magnification off mode). In particular, when the output control unit 46 determines that the endoscope images are not being observed in the magnified mode, the output control unit 46 outputs the latest scene recognition result of the scene recognition results retained in the memory 47.

In the example illustrated in FIG. 10, three successive frames of endoscope images are being observed in the magnified mode (i.e., magnification on mode), so that the scene recognition result ("stomach") prior to the three frames, serving as the latest scene recognition result in which the endoscope image is determined as being not observed in the magnified mode (magnification off mode), is output.

It is preferable that an upper limit be provided for the retained number of scene recognition results sequentially retained in the memory 47, such that when the retained number exceeds the upper limit, a scene recognition result retained in the memory 47 is deleted, starting from an older scene recognition result.

Third Embodiment of Output Control Process

FIG. 11 illustrates a second embodiment of, for example, scene recognition results retained in the memory.

As illustrated in FIG. 11, the memory 47 retains scene recognition results including reliability levels of multiple respective scenes (i.e., four scenes of the "pharynx", "esophagus", "stomach", and "duodenum") and magnification information (i.e., magnification on/off information) in association with each other in chronological order.

If the output control unit 46 performing the output control process according to the third embodiment determines that an endoscope image is not being observed in the magnified mode based on the magnification information (magnification on/off information) acquired by the magnification information acquisition unit 44, the output control unit 46 calculates an average value of the reliability levels for each scene retained in the memory 47 illustrated in FIG. 11 and outputs, as a scene recognition result, a scene to which the largest average value of the average values belongs. According to the reliability levels of each of the four scenes retained in the memory 47 illustrated in FIG. 11, the average value of the reliability levels of the "stomach" is the largest, so that the output control unit 46 outputs the scene recognition result indicating the "stomach".

As a modification of the third embodiment of the output control process, the output control unit 46 reduces the weight of the reliability level corresponding to when an endoscope image is determined as being observed in the magnified mode based on the magnification information (i.e., the magnification on/off information) among the reliability levels of each of the four time-series scenes retained in the memory 47 illustrated in FIG. 11, calculates an average load value of the reliability levels for each of the four scenes, and outputs, as a scene recognition result, a scene to which the largest average load value of the average load values belongs.

It is preferable that an upper limit be provided for the retained number of scene recognition results including the reliability levels for each of the four scenes and pieces of magnification information that are sequentially retained in the memory 47, such that when the retained number exceeds the upper limit, the scene recognition results including the reliability levels for each scene and the magnification information retained in the memory 47 are deleted, starting from an older scene recognition result and older magnification information. The average value or the average load value of the reliability levels for each of the four scenes is calculated by using the reliability levels for the respective scenes corresponding to the retained number in the memory 47.

The scene recognition results output-controlled by the output control unit 46 can be displayed on the display unit 16 together with the endoscope images sequentially displayed on the display unit 16. Specifically, the information display control unit 45B can acquire each output-controlled scene recognition result from the output control unit 46 and, for example, display the scene recognition result at a position other than the display region of the endoscope image. Accordingly, the user can check whether the observed organ in the normal observation mode or the magnified observation mode is either the "pharynx", "esophagus", "stomach", or "duodenum".

When a still image of an endoscope image is to be stored in the memory 47 or an external memory, the scene recognition result output-controlled by the output control unit 46 can be added as accessory information of the endoscope image to be stored.

Furthermore, the output control unit 46 can output the output-controlled scene recognition result to an external device. Conceivable examples of the external device include recognition units that are provided for the respective organs including the "pharynx", "esophagus", "stomach", and "duodenum" and that each receive an endoscope image and detect a region-of-interest, such as a lesion, from the endoscope image. In accordance with the scene recognition result output-controlled by the output control unit 46, a recognition unit serving as an output destination for the endoscope image can be selected.

In this example, the scenes to be recognized by the scene recognition unit 42 are the four scenes (i.e., the types of organs) of the "pharynx", "esophagus", "stomach", and "duodenum". Alternatively, based on an endoscope image, the scene recognition unit 42 may recognize, for example, at least one of a section of an organ within the body, the presence or absence of *Helicobacter pylori*, a range diagnosis of a lesion, the image quality, or whether or not the image is appropriate for an image diagnosis.

Endoscope Image Processing Method

Figure 12:
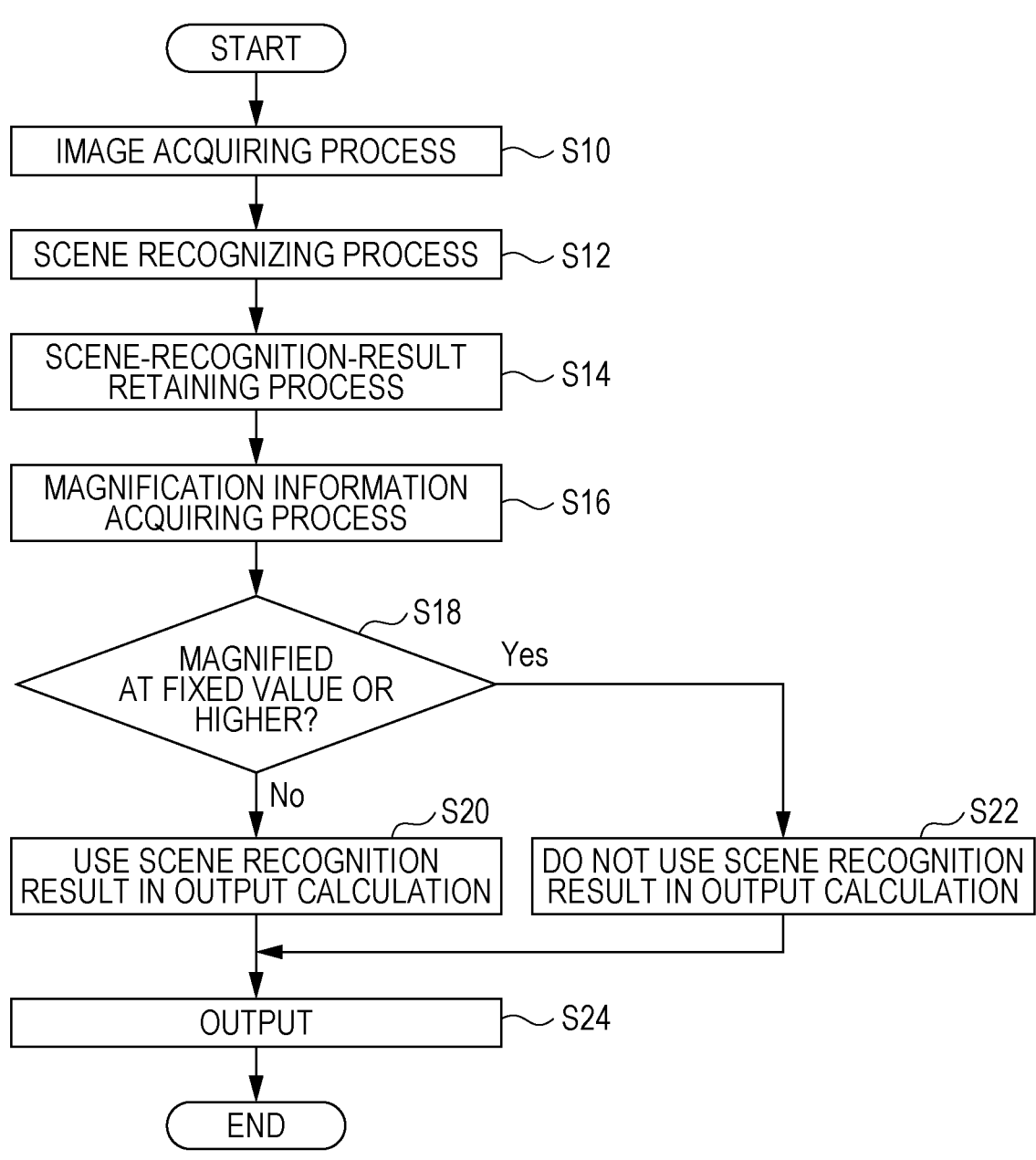
FIG. 12 is a flowchart illustrating an endoscope image processing method according to an embodiment of the present invention.

FIG. 12 is a flowchart illustrating an endoscope image processing method according to an embodiment of the present invention, and relates to a procedure performed by the units of the endoscope image processing apparatus 14 illustrated in FIG. 2.

In FIG. 12, the CPU 41 causes the endoscope image acquisition unit 40 to acquire one frame of endoscope image 38a from time-series endoscope images 38a in step S10.

In step S12 (scene recognition step), the CPU 41 causes the scene recognition unit 42 to perform a scene recognizing process of recognizing a scene of the endoscope image 38a based on the endoscope image 38a. In this example, the scene recognition unit 42 recognizes whether a hollow organ image-captured by the endoscope 10 serving as an upper gastrointestinal scope is of any of multiple types (i.e., the pharynx, esophagus, stomach, and duodenum).

Then, in step S14 (scene-recognition-result retaining step), the scene-recognition-result retention processing unit 43 causes the memory 47 to retain a scene recognition result of the endoscope image 38a obtained in step S12. For example, the scene-recognition-result retention processing unit 43 can cause the memory 47 to retain scene recognition results and magnification information (magnification on/off information) in chronological order, as illustrated in FIG. 10, or can cause the memory 47 to retain scene recognition results including the reliability levels for each of the four scenes of the "pharynx", "esophagus", "stomach", and "duodenum" and magnification information (magnification on/off information) in association with each other in chronological order, as illustrated in FIG. 11.

An upper limit is provided for the retained number in the memory 47, so that when the memory 47 is caused to retain, for example, a new scene recognition result in step S14, the oldest scene recognition result is deleted.

Subsequently, in step S16 (magnification information acquiring step), the CPU 41 causes the magnification information acquisition unit 44 to execute a magnification information acquiring process of acquiring magnification information related to a magnification ratio of the endoscope image 38a acquired in step S10 or whether or not the endoscope image 38a is magnified. As illustrated in FIG. 5A, FIG. 5B, FIG. 6A, and FIG. 6B, the magnification scale 50 or 52 indicating the magnification ratio of the endoscope image 38a is created and is displayed on the display unit 16, so that the magnification information acquisition unit 44 can acquire the magnification ratio from the endoscope system 9 that creates the magnification scale 50 or 52, or can acquire the magnification ratio from the endoscope image 38a to which the magnification scale 50 or 52 is added.

Then, in step S18, the CPU 41 determines whether or not the endoscope image 38a is magnified at a fixed value or higher based on the magnification information of the endoscope image 38a acquired in step S16. The fixed value is a threshold value of the magnification ratio used for determining whether the endoscope image 38a is observed in the normal observation mode or the magnified observation mode.

If it is determined in step S18 that the endoscope image 38a is not magnified at the fixed value or higher ("No"), the output control unit 46 uses the scene recognition result obtained in step S14 for an output calculation and sets a scene recognition result to be ultimately output based on a scene-recognition-result setting method in step S20 (output control step). In this case, based on the scene-recognition-result setting method, the output control unit 46 can calculate the scene recognition result by using, for example, a scene recognition result retained in the memory 47 in place of using the scene recognition result obtained in step S14.

In contrast, if it is determined in step S18 that the endoscope image 38a is magnified at the fixed value or higher ("Yes"), the output control unit 46 sets a scene recognition result to be ultimately output in step S22 (output control step) based on the scene-recognition-result setting method without using the scene recognition result obtained in step S14 for the output calculation. In this case, based on the scene-recognition-result setting method, the output control unit 46 can calculate the scene recognition result by using, for example, a scene recognition result retained in the memory 47 in the past.

Conceivable examples of a method of calculating a scene recognition result to be ultimately output based on the scene-recognition-result setting method include the output control processes according to the first embodiment to the third embodiment described with reference to FIG. 10 and FIG. 11. The scene-recognition-result setting method may be set in advance or may be selected by the user.

In step S24, the output control unit 46 outputs the output-controlled scene recognition result calculated in step S20 or step S22 to, for example, the display control unit 45 of the endoscope image processing apparatus 14 or to the external device.

The process from step S10 to step S24 corresponds to a process performed on the current single frame of the time-series endoscope images 38a, and is repeatedly performed on each of the endoscope images 38a to be sequentially acquired.

Other Features

As an alternative to the above embodiment in which the endoscope processor and the endoscope image processing apparatus are provided separately from each other, the endoscope processor and the endoscope image processing apparatus may be integrated with each other. Specifically, the endoscope processor may be provided with the function of the endoscope image processing apparatus.

The hardware structure that executes various kinds of control in the endoscope image processing apparatus according to the above embodiment includes various types of processors indicated below. The various types of processors include a central processing unit (CPU) serving as a general-purpose processor functioning as various types of control units by executing software (program), a programmable logic device (PLD), such as a field programmable gate array (FPGA), serving as a processor whose circuit configuration is changeable after being manufactured, and a dedicated electric circuit, such as an application specific integrated circuit (ASIC), serving as a processor having a circuit configuration designed specifically for executing a specific process.

One processing unit may be constituted of one of these various types of processors, or may be constituted of two or more of processors of the same type or different types (e.g., multiple FPGAs or a combination of a CPU and an FPGA). Furthermore, multiple control units may be constituted of a single processor. As a first example where multiple control units are constituted of a single processor, a single processor is constituted of a combination of at least one CPU and software, as represented by a client computer or a server computer, and this processor functions as multiple control units. In a second example, a processor that realizes the function of the entire system including multiple control units by using a single integrated circuit (IC) chip is used, as represented by a system-on-chip (SoC). Accordingly, the various types of control units are constituted of one or more of the aforementioned various types of processors as the hardware structure.

Furthermore, the present invention includes an endoscope image processing program that is installed in a computer to cause the computer to function as the endoscope image processing apparatus according to the present invention, and also includes a nonvolatile storage medium storing the endoscope image processing program.

Moreover, the present invention is not limited to the above embodiment, and permits various modifications so long as they do not depart from the spirit of the present invention.

REFERENCE SIGNS LIST

9 endoscope system
10 endoscope
11 light source device
12 endoscope processor
13 display device
14 endoscope image processing apparatus
15 operating unit
16 display unit
20 insertion section
21 handheld operation section
22 universal cord
25 soft part
26 bending part
27 tip part
28 imaging element
29 bending knob
30 air/water supply button
31 suction button
32 still-image capture command part
33 treatment tool inlet
35 light guide
36 signal cable
37a, 37b connector
38 motion picture
38a endoscope image
39 still image
40 endoscope image acquisition unit
41 CPU
42 scene recognition unit
42A input layer
42B interlayer
42C output layer
43 scene-recognition-result retention processing unit
44 magnification information acquisition unit
45 display control unit
45A image display control unit
45B information display control unit
46 output control unit
47 memory
50, 52 magnification scale
S10 to S24 step

What is claimed is:

1. An endoscope image processing apparatus comprising a processor,
wherein the processor is configured to execute:
an endoscope image acquiring process of acquiring a time-series endoscope image;
a scene recognizing process of recognizing a scene based on the endoscope image;

a scene-recognition-result retaining process of causing a retaining unit to retain a scene recognition result of the recognized scene;

a magnification information acquiring process of acquiring magnification information from an endoscope system or the endoscope image, the magnification information being related to a magnification ratio of the endoscope image or whether or not the endoscope image is magnified; and an output control process of controlling and outputting the scene recognition result retained in the retaining unit based on the acquired magnification information, wherein the output control process sets a scene recognition result to be ultimately output from the scene recognition result retained in the retaining unit, the scene recognition result to be ultimately output being set based on the magnification information and a method for setting the scene recognition result, wherein the output control process outputs, if the endoscope image is determined as being observed in a magnified mode based on the magnification information, the scene recognition result retained in the retaining unit and corresponding to when the endoscope image is determined as being not observed in the magnified mode.

2. The endoscope image processing apparatus according to claim 1, wherein the scene-recognition-result retaining process causes the retaining unit to retain the magnification information together with the scene recognition result.

3. The endoscope image processing apparatus according to claim 1, wherein the scene-recognition-result retaining process causes the retaining unit to retain the scene recognition result on a time-series basis.

4. The endoscope image processing apparatus according to claim 1, wherein the processor is configured to perform a process of generating a display image in which the magnification information is added to a specific position other than a display region of the endoscope image, and wherein the magnification information acquiring process acquires the magnification information by reading the magnification information at the specific position from the display image.

5. The endoscope image processing apparatus according to claim 1, wherein the magnification information acquiring process acquires the magnification information from the processor.

6. The endoscope image processing apparatus according to claim 1, wherein the output control process outputs a latest scene recognition result retained in the retaining unit when the endoscope image is determined as being not observed in the magnified mode based on the magnification information.

7. The endoscope image processing apparatus according to claim 1, wherein the scene-recognition-result retaining process causes the retaining unit to retain the scene recognition result on a time-series basis, the scene recognition result including a reliability level for each of a plurality of scenes, and wherein the output control process outputs, as the scene recognition result, a scene to which a highest reliability level of the reliability levels of the respective scenes belongs, the scene being retained in the retaining unit when the endoscope image is determined as not being observed in the magnified mode based on the magnification information.

8. The endoscope image processing apparatus according to claim 1, wherein the scene-recognition-result retaining process causes the retaining unit to retain the scene recognition result on a time-series basis, the scene recognition result including a reliability level for each of a plurality of scenes, and wherein the output control process calculates an average value of reliability levels for each scene and outputs, as the scene recognition result, a scene to which a largest average value of the average values belongs, the scene being retained in the retaining unit when the endoscope image is determined as not being observed in the magnified mode based on the magnification information.

9. The endoscope image processing apparatus according to claim 1, wherein the scene-recognition-result retaining process causes the retaining unit to retain the scene recognition result on a time-series basis, the scene recognition result including a reliability level for each of a plurality of scenes, and wherein the output control process reduces a weight of the reliability level corresponding to when the endoscope image is determined as being observed in the magnified mode based on the magnification information among the reliability levels of the respective scenes retained on the time-series basis in the retaining unit, calculates an average load value of the reliability level of each scene, and outputs, as the scene recognition result, a scene to which a largest average load value of the average load values belongs.

10. The endoscope image processing apparatus according to claim 1, wherein the scene-recognition-result retaining process provides an upper limit for a retained number of scene recognition results obtained in the scene recognizing process and retained in the retaining unit, and deletes the scene recognition result retained in the retaining unit, starting from an older scene recognition result, when the retained number exceeds the upper limit.

11. The endoscope image processing apparatus according to claim 1, wherein the scene recognizing process recognizes, based on the endoscope image, at least one of a type of an organ within a body, a section of an organ within a body, presence or absence of *Helicobacter pylori*, a range diagnosis of a lesion, image quality, or whether or not an image is appropriate for an image diagnosis.

12. An endoscope image processing method for causing a processor to execute a process comprising:

a step for acquiring a time-series endoscope image;

a scene recognizing step for recognizing a scene based on the endoscope image;

a scene-recognition-result retaining step for causing a retaining unit to retain a scene recognition result of the recognized scene;

a magnification information acquiring step for acquiring magnification information from an endoscope system or the endoscope image, the magnification information being related to a magnification ratio of the endoscope image or whether or not the endoscope image is magnified; and an output control step for controlling and outputting the scene recognition result retained in the retaining unit based on the acquired magnification information, wherein the output control step sets a scene recognition result to be ultimately output from the scene recognition result retained in the retaining unit, the scene recognition result being set based on the magnification information and a method for setting the scene recognition result, wherein the output control step outputs, if the endoscope image is determined as being observed in a magnified mode based on the magnification information, the scene recognition result retained in the retaining unit and corresponding to when the endoscope image is determined as being not observed in the magnified mode.

13. The endoscope image processing method according to claim 12, wherein the scene-recognition-result retaining step causes the retaining unit to retain the magnification information together with the scene recognition result.

14. The endoscope image processing method according to claim 12, wherein the scene-recognition-result retaining step causes the retaining unit to retain the scene recognition result on a time-series basis.

15. The endoscope image processing method according to claim 12, further comprising:

a step for generating a display image in which the magnification information is added to a specific position other than a display region of the endoscope image, and wherein the magnification information acquiring step acquires the magnification information by reading the magnification information at the specific position from the display image.

16. The endoscope image processing method according to claim 12, further comprising:

a step for generating a display image in which the magnification information is added to a specific position other than a display region of the endoscope image, and wherein the magnification information acquiring step acquires the magnification information from the processor that adds the magnification information to the display image.

17. A non-transitory, computer readable tangible storage medium storing a program for causing, when read by a computer, the computer to execute the endoscope image processing method according to claim 12.

* * * * *